(12) United States Patent
Järpenberg et al.

(10) Patent No.: US 7,642,398 B2
(45) Date of Patent: Jan. 5, 2010

(54) ELASTICIZED WEB AND A METHOD AND APPARATUS FOR ITS MANUFACTURE

(75) Inventors: Christian Järpenberg, Landvetter (SE); Michael Linder, Göteborg (SE); José-Maria Mansisidor, Mölnlycke (SE); Åsa Lindström, Göteborg (SE); Karin Lindmark, Göteborg (SE); Ingemar Fernfors, Mölndal (SE); Kenneth Strannemalm, Floda (SE)

(73) Assignee: SCA Hygiene Products AB, Gothenburg (SE)

( * ) Notice: Subject to any disclaimer, the term of this patent is extended or adjusted under 35 U.S.C. 154(b) by 789 days.

(21) Appl. No.: 10/327,863

(22) Filed: Dec. 26, 2002

(65) Prior Publication Data

US 2003/0144643 A1 Jul. 31, 2003

Related U.S. Application Data

(60) Provisional application No. 60/342,752, filed on Dec. 28, 2001.

(30) Foreign Application Priority Data

Dec. 28, 2001 (SE) .................................. 0104466

(51) Int. Cl.
 *A61F 13/15* (2006.01)
 *A61F 13/20* (2006.01)
(52) U.S. Cl. ........................ 604/378; 604/367
(58) Field of Classification Search ................ 604/358, 604/366, 378, 382, 385.01, 385.1, 368; 442/327, 442/352, 394, 366; 428/131, 141, 198, 103, 428/152, 114, 167, 170, 171, 218
See application file for complete search history.

(56) References Cited

U.S. PATENT DOCUMENTS

| | | | |
|---|---|---|---|
| 3,879,256 A | 4/1975 | Rust, Jr. | |
| 4,333,978 A | 6/1982 | Kocher | |
| 4,355,425 A | 10/1982 | Jones et al. | |
| 4,556,596 A | 12/1985 | Meuli | |
| 4,720,415 A | 1/1988 | Vander Wielen et al. | |
| 6,291,039 B1 | 9/2001 | Combe et al. | |
| 6,733,610 B2 * | 5/2004 | Mizutani et al. | 156/164 |
| 6,803,334 B2 * | 10/2004 | Mizutani et al. | 442/394 |

FOREIGN PATENT DOCUMENTS

EP 0 023 084 2/1981

(Continued)

OTHER PUBLICATIONS

Office Action dated Feb. 23, 2009 issued in corresponding Japanese Patent Application No. 2003-559749.

*Primary Examiner*—Michele Kidwell
(74) *Attorney, Agent, or Firm*—Buchanan Ingersoll & Rooney PC

(57) ABSTRACT

An elasticized web has a gatherable substrate and a multi-strand elastic yarn affixed to the gatherable substrate at a plurality of fixation locations. So that the yarn can be affixed to the substrate without the use of an adhesive, the yarn is subjected to forces to create partial delamination of the yarn at the fixation locations and a portion of the gatherable substrate is caused to pass between the thus delaminated strands of the multi-strand elastic yarn. The elasticized web of the present invention is particularly suitable for use in disposable absorbent articles.

51 Claims, 8 Drawing Sheets

FOREIGN PATENT DOCUMENTS

| | | |
|---|---|---|
| EP | 0 084 903 A2 | 8/1983 |
| EP | 0 217 032 B1 | 4/1987 |
| EP | 0 474 123 | 3/1992 |
| EP | 0 596 191 A1 | 5/1994 |
| EP | 0 685 586 A2 | 12/1995 |
| EP | 0 713 546 | 3/1997 |
| EP | 1 035 818 | 4/2002 |
| JP | S56-025441 | 3/1981 |
| JP | S58-171957 | 10/1983 |
| JP | S61-137730 | 6/1986 |
| JP | S62-033889 | 2/1987 |
| JP | H03-505046 | 12/1991 |
| JP | H08-058007 | 3/1995 |
| JP | H08-132576 | 5/1996 |
| JP | H08-504136 | 5/1996 |
| JP | H10-501195 | 2/1998 |
| JP | 2001-504899 | 4/2001 |
| WO | 89/09550 | 10/1989 |
| WO | 94/05241 | 3/1994 |
| WO | WO 95/34264 A1 | 12/1995 |
| WO | 97/34506 | 9/1997 |
| WO | WO 97/34506 A1 | 9/1997 |
| WO | 99/27876 | 6/1999 |
| WO | 00/37003 | 6/2000 |
| WO | 00/37005 | 6/2000 |

\* cited by examiner

ELASTICIZED WEB AND A METHOD AND APPARATUS FOR ITS MANUFACTURE

CROSS-REFERENCE TO RELATED APPLICATIONS

The present application claims the priority under 35 U.S.C. §119 of U.S. Provisional Application No. 60/342,752, filed in the United States on Dec. 28, 2001, and to Swedish Application No. 0104466-8, filed in Sweden on Dec. 28, 2001, the entire contents of both applications are hereby incorporated herein by reference.

BACKGROUND

1. Technical Field

The present invention relates to an elasticized web comprising a gatherable substrate and a multi-strand elastic yarn for use primarily, though not exclusively, in absorbent articles such as diapers and incontinence garments. The invention further relates to a method and apparatus for manufacturing an elasticized web.

2. Background of the Invention

It is known to produce elasticized webs in a number of different ways. Traditionally, an elastic yarn is elongated under a tensioning force and is affixed using adhesive to a non-tensioned substrate which is to be gathered. The adhesive may be applied either to the elongated elastic yarn at discrete locations along the yarn before the elongated yarn is made to contact the substrate which is to be gathered, or the adhesive may be applied in a predetermined pattern, such as in a grid or helical fashion, to the substrate. Alternatively, the adhesive may be applied to both. Irrespective of how and where the adhesive is applied, the elongated yarn bonds to the substrate at discrete locations and, when the tensioning force is removed, the elastic yarn tends to contract back towards its original, non-tensioned length, thereby gathering the substrate.

While the above-described method has been widely adopted, it suffers from several drawbacks. Firstly, due to its inherent stickiness, the use of any adhesive in a production process requires that the adhesive be accurately metered at exact locations, otherwise components of the production machinery, as well as undesired regions of the article of manufacture, may become contaminated by the adhesive. Secondly, in fluid permeable articles, adhesive tends to reduce the breathability of the article, something which is clearly disadvantageous in articles such as disposable diapers. Thirdly, adhesive acts as a barrier to the transport of liquid, again possibly to the detriment of article such as disposable diapers. Fourthly, adhesive tends to stiffen an article, i.e. those regions of an article in which adhesive is present are less flexible than those regions having no adhesive. Fifthly, adhesive is an additional component which must be procured and handled, thereby contributing to the production costs of the manufactured article.

In an attempt to overcome at least some of these drawbacks, a method of producing an elasticized web without the use of adhesive is disclosed in WO-A-97/34506. According to this document, an elastic yarn passes in a stretched condition through a sleeve formed by a substrate which is to be gathered. At spaced locations along the yarn, connecting portions are formed in the sleeve on radially opposed sides of the yarn. The connecting portions define a passage of restricted size through which the elastic yarn in its stretched condition can pass due to its decreased diameter in the stretched condition. These connection portions are produced by passing the sleeve and stretched elastic yarn between a pair of rollers. One roller is provided about its periphery with a plurality of sets of axially opposed raised heels. The gap between the sets of axially opposed raised heels defines a peripheral channel with which the elastic yarn is aligned. The heels are arranged to generate heat, for example by ultrasound, such that, as each set of opposed heels contacts the sleeve formed by the substrate, heat fusion of the material of the sleeve takes place, thereby forming the connection portions. Once tension in the yarn is released, the diameter of the yarn tends to revert to its non-tensioned dimension. However, those portions of the yarn in the passages between the connecting portions are unable to expand due to the restriction created by the opposed connecting portions. The radial expansion of the yarn either side of each pair of connecting portions effectively immobilizes the yarn in the connecting portions. Thus, as the yarn contracts in the axial direction, it gathers the substrate to thereby create an elasticized web.

Although the elasticized web produced in accordance with WO-A-97/34506 does not suffer from the drawbacks associated with adhesively attached elastic yarns, its method of manufacture nevertheless makes it unattractive for certain mass production applications, particularly for disposable absorbent articles. A major disadvantage is the need for very close tolerances to create the passage of restricted size between the opposed connecting portions. A further disadvantage is that, for each different diameter of yarn which is to be employed, a corresponding pair of rollers is required. Furthermore, since the diameter of an elastic yarn is dependent on the degree of elongation of the yarn, a separate pair of rollers is required for each desired amount of elongation of one and the same elastic yarn. In addition, the method according to WO-A-97/34506 is not easily adaptable for products having a plurality of relatively closely spaced elastic yarns. This is due to the fact that each yarn must be located in its own peripheral channel during manufacture of the elasticized web. In addition, only rectilinear lines of connection would seem to be able to be formed using the above-described method, thereby excluding the possibility of laying out the elastic yarn in a curved path. Finally, the connection between the elastic yarn and the substrate relies entirely on friction.

OBJECTS AND SUMMARY

It is therefore an object of the present invention to provide an elasticized web in which improved attachment is attained between the elastic yarn and the gatherable substrate without the need for an adhesive.

In its broadest form, this object is achieved by the elasticized web as claimed in claim 1 in which the elasticized web comprises a first gatherable substrate and a multi-strand elastic yarn affixed to the first gatherable substrate at a number of first fixation locations. At each first fixation location, a portion of the first gatherable substrate passes between strands of the multi-strand elastic yarn.

Since a portion of the substrate passes between strands of the yarn, an interlocking mechanical fixation is attained.

In accordance with a further aspect of the present invention an elasticized web is provided as claimed in independent claim 4 in which the elasticized web comprises two gatherable substrates and a multi-strand elastic yarn located between the two gatherable substrates. The multi-strand elastic yarn is affixed to the two gatherable substrates at a number of first fixation locations. At each first fixation location, a portion of at least one of the two substrates passes between strands of the multi-strand elastic yarn such that the two gatherable substrates are joined together at each first fixation location. Since, in accordance with this aspect of the invention, the two substrates either side of the elastic yarn are joined together through the yarn, a substantially permanent fixation between the yarn and substrates is ensured.

It is a further object of the present invention to provide a disposable absorbent article which can contain less adhesive than conventional comparable absorbent articles.

This object is achieved in its broadest form by the disposable absorbent article as claimed in claim 20 and by a disposable absorbent article for attachment around the waist of a wearer as claimed in claim 22.

Since the disposable absorbent article according to the present invention comprises an absorbent structure including at least one region comprising an elasticized web of one aspect of the present invention, and such an elasticized web requires no adhesive, the disposable absorbent article of the invention contains less adhesive than a comparable conventional absorbent article in which adhesive is required to create an elasticized web.

It is yet a further object of the present invention to provide a method for manufacturing an elasticized web in which adequate attachment between the elastic yarn and the gatherable substrate(s) is attained without the need for an adhesive.

This object is attained by the methods as claimed in independent claims 36 and 37, respectively.

The methods according to the present invention are based on the recognition that a multi-strand elastic yarn partially delaminates when subjected to stress. In other words, if a multi-strand elastic yarn is subjected to, for example, a pressure and/or tensioning force, some of the strands of the yarn will delaminate and create gaps in the yarn through which a portion of one (or both) of the gatherable substrates can be made to pass. As is explained above, in this manner an interlocking mechanical fixation is attainable.

It is still a further object of the present invention to provide apparatus for manufacturing an elasticized web, which apparatus does not require any provision for supplying adhesive to the elastic yarn or the substrate.

This object is achieved by the apparatus as claimed in independent claims 46 and 47, respectively.

Preferred embodiments of the elasticized webs, disposable absorbent articles, the methods of manufacture and the apparatus according to the invention are detailed in the dependent claims.

BRIEF DESCRIPTION OF THE DRAWINGS

The invention will be described in the following by way of example only and with reference to the attached drawings, in which.

DETAILED DESCRIPTION OF PREFERRED EMBODIMENTS

Figure 1:
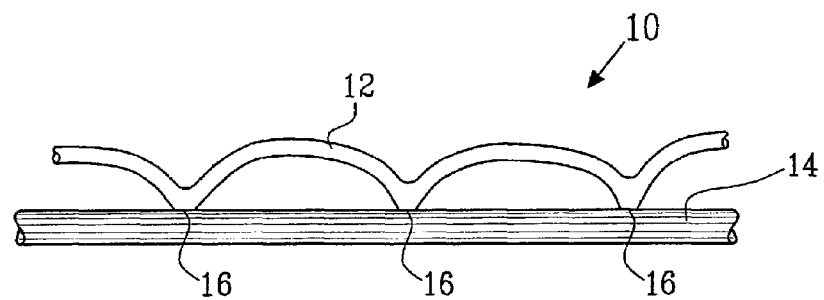
FIG. 1 is a schematic cross-sectional view through a portion of an elasticized web according to a first embodiment of the present invention.
Figure 3:
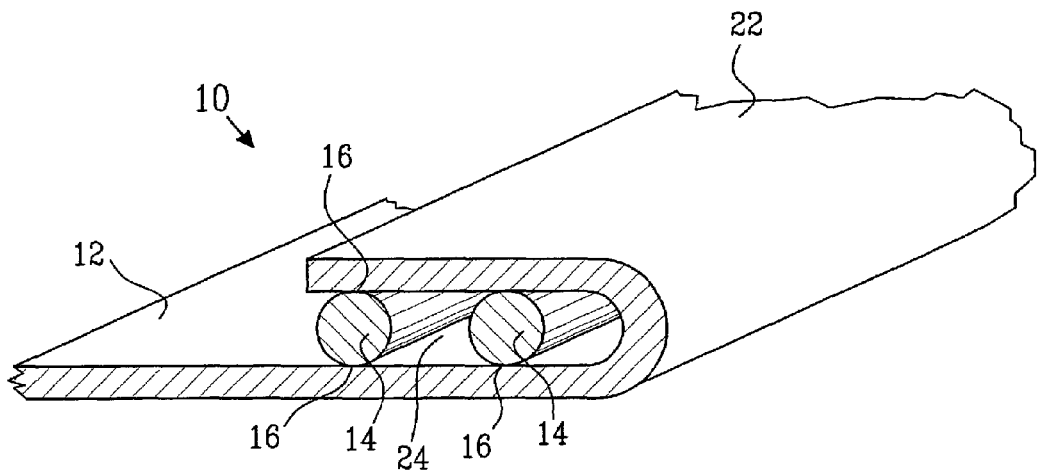
FIG. 3 is a schematic cross-sectional view through a portion of an elasticized web according to a second embodiment of the present invention.

In the drawings, reference numeral 10 generally denotes an elasticized web according to the present invention. With particular reference to FIGS. 1 and 3, the elasticized web 10 comprises a first gatherable substrate 12 and a multi-strand elastic yarn 14 affixed to the first gatherable substrate at a number of first fixation locations 16.

At least in so far as the present invention is concerned, the expression "multi-strand elastic yarn" means a yarn made up of a plurality of strands (also known as filaments) arranged in parallel and laminated together such that, in an initial unstretched condition, each strand of a majority of the strands contacts at least two further strands. A suitable multi-strand elastic yarn 14 is shown in greater detail in the photographs of FIG. 2. The illustrated yarn is a multi-strand elastic yarn sold under the trade name LYCRA® XA® in this case of 540 dtex. It is of course to be understood that any suitable multi-strand elastic yarn may be employed in the present invention. Further examples of suitable yarn include Dorlastan® from Bayer AG and Linel® from Fillatice.

The principles underlying the present invention are based on the recognition that a multi-strand elastic yarn partially delaminates when subjected to stress. In other words, if a multi-strand elastic yarn is subjected to, for example, a pressure and/or tensioning force, some of the strands of the yarn will delaminate and create gaps through the yarn. The present invention utilizes at least some of these gaps as openings through which a portion of a gatherable substrate can be made to pass.

Figure 2:
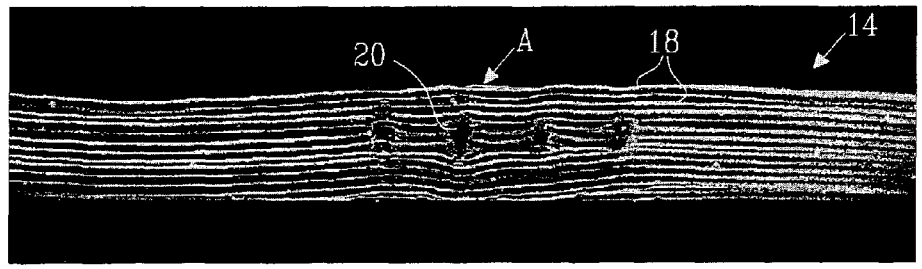
FIG. 2 is a photographic representation on a scale of 50:1 of a multi-strand elastic yarn suitable for use in the elasticized web of the present invention.

In FIG. 2, the LYCRA® yarn has been elongated 200% of its initial, non-tensioned length, i.e. to three times its original length, and subjected to a source of ultrasonic energy directed on the region denoted by arrow A. It will be observed that, in the region A, a number of strands 18 of the yarn 14 have parted from adjacent strands to create gaps 20, i.e. the yarn 14 has at least partially delaminated. Although the LYCRA® yarn illustrated in FIG. 2 has been subjected to a source of ultrasonic energy, it is to be understood that the invention can be practiced using any type of energy source which will cause the multi-strand elastic yarn to delaminate in the above-described fashion.

In accordance with a first aspect of the present invention, at each first fixation location 16, a portion of the first gatherable substrate 12 passes between strands 18 of the multi-strand elastic yarn 14 into one or more gaps 20. Since a portion of the substrate passes between strands of the yarn, an interlocking mechanical fixation is attained.

What constitutes a "portion" of the substrate is dependent on the material of the substrate. If the substrate is made from a fibrous material, then the portion of the substrate which passes between the strands of the elastic yarn may simply be some fibers of the substrate. Preferably, the first gatherable substrate comprises a thermally bondable material. In such case, the portion of the first gatherable substrate may comprise a melted component of the gatherable substrate. The thermally bondable material of the gatherable substrate is advantageously selected from the group consisting of a spunbond, air laid, wet laid, hydroentangled, needled, carded or meltblown nonwoven of polyester, polypropylene, polyethylene or the like. Alternatively, the thermally bondable material may be a combination of polymers, either mixed or in layers. A bi-component fiber, preferably of polyethylene covered polypropylene or polypropylene/polyethylene side-by-side fiber, can also be used.

The present invention may also be practiced on non-fibrous thermally bondable materials. In such cases, the thermally bondable material is advantageously a thermoplastic elastomer of polyurethane in sheet or film form.

In yet another embodiment of the present invention, the gatherable substrate may be constituted by a laminate material which displays elastic properties itself. Examples of such laminate materials are to be found in U.S. Pat. No. 4,355,425 and U.S. Pat. No. 4,556,596. Preferably, the elastic laminate material is an elastic nonwoven laminate of the type disclosed, for example, in EP-B-0 713 546. It is accordingly conceivable that it be desirable to provide selected regions of such a laminate with greater elastification than other regions of the laminate. In a non-limiting example, the elastic nonwoven laminate may be used as a cover layer in a diaper. By providing elastic yarns around, for example, the waist and leg openings, but not in remaining regions of the cover layer, greater elasticity will be imparted to the waist and leg opening regions.

Although, in theory, the present invention may be realized using any multi-strand elastic yarn capable of delaminating under stress, and thereby any substrate which is capable of being gathered by such yarn, the present inventors have found that, at least for the preferred field of application, i.e. garments to be worn, a suitable gatherable substrate has a basis weight of from 5 to 80 g/m$^2$, preferably from 10 to 40 g/m, more preferably from 10 to 30 g/m$^2$ and most preferably from 15 to 25 g/m$^2$.

A further embodiment of the elasticized web of the present invention is illustrated in FIG. 3 in which a region 22 of the first gatherable substrate 12 is folded over the multi-strand elastic yarn 14 to form a pocket 24 within which the multi-strand elastic yarn runs. In such an embodiment, the elastic yarn is advantageously affixed to the gatherable substrate at fixation locations 16 on radially opposed sides of the elastic yarn to thereby also affix the yarn to the folded over region 22 of the substrate. Naturally, and as illustrated, more than one elastic yarn may be provided in the pocket 24.

Figure 4:
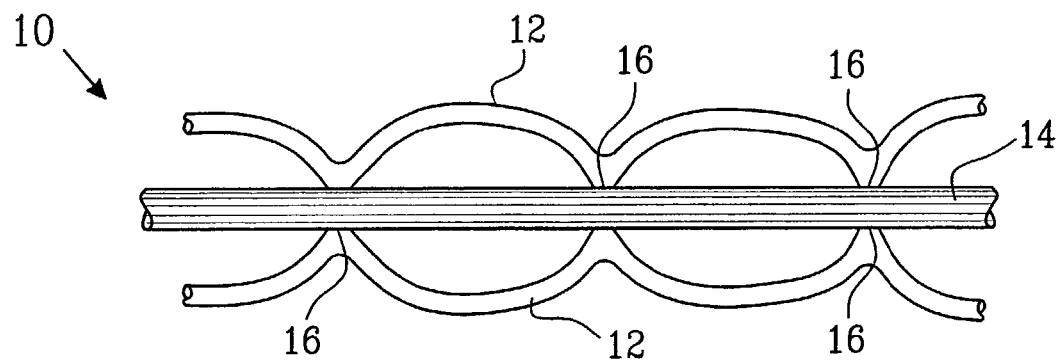
FIG. 4 is a schematic cross-sectional view through a portion of an elasticized web according to a third embodiment of the present invention.

In the foregoing, an elasticized web comprising just one gatherable substrate has been described. Nevertheless, and as will be apparent from FIG. 4, the present invention also contemplates various embodiments of elasticized webs comprising two or more gatherable substrates. It is to be understood that each gatherable substrate of such multi-substrate webs may comprise any of the materials disclosed above for the first gatherable substrate. The various gatherable substrates of multi-substrate webs may be of the same or differing material and have the same, similar or different basis weights. Although, for the sake of clarity and conciseness, not all the conceivable material combinations are expressly recited, it is to be understood that the disclosure herein is intended to embrace all such combinations.

Thus, according to a second aspect of the present invention, an elasticized web 10 is provided comprising two gatherable substrates 12 and a multi-strand elastic yarn 14 located between the two gatherable substrates. The elastic yarn 14 is affixed to the two gatherable substrates at a number of first fixation locations 16. At each first fixation location a portion of at least one of the two substrates passes between strands of the multi-strand elastic yarn such that the two gatherable substrates are joined together at each first fixation location. In this respect, the term "joined together" is intended to embrace situations in which the two gatherable substrates are in direct contact with each other by means of a portion of one of the substrates passing between strands of the elastic yarn to contact a portion or portions of the second substrate, as well as by means of a portion of each of the substrates passing between strands of the elastic yarn to contact corresponding or other portions of the other substrate. The term "joined together" also covers the situation in which the substrates are not in direct contact with each other at the first fixation locations 16, but are instead joined via the elastic yarn. In other words, a portion of one or both of the gatherable substrates passes between strands of the elastic yarn without the portion of one substrate contacting any portion of the other substrate.

Preferably, at least one of the two gatherable substrates 12 comprises a thermally bondable material. Advantageously, the portion of at least one of the two substrates which passes between strands of the elastic yarn 14 comprises a melted component of the at least one of the two gatherable substrates comprising the thermally bondable material. A particularly advantageous embodiment is attained when both gatherable substrates comprise a thermally bondable material and attachment at the first fixation locations is attained by melting a portion of both substrates.

Figure 5:
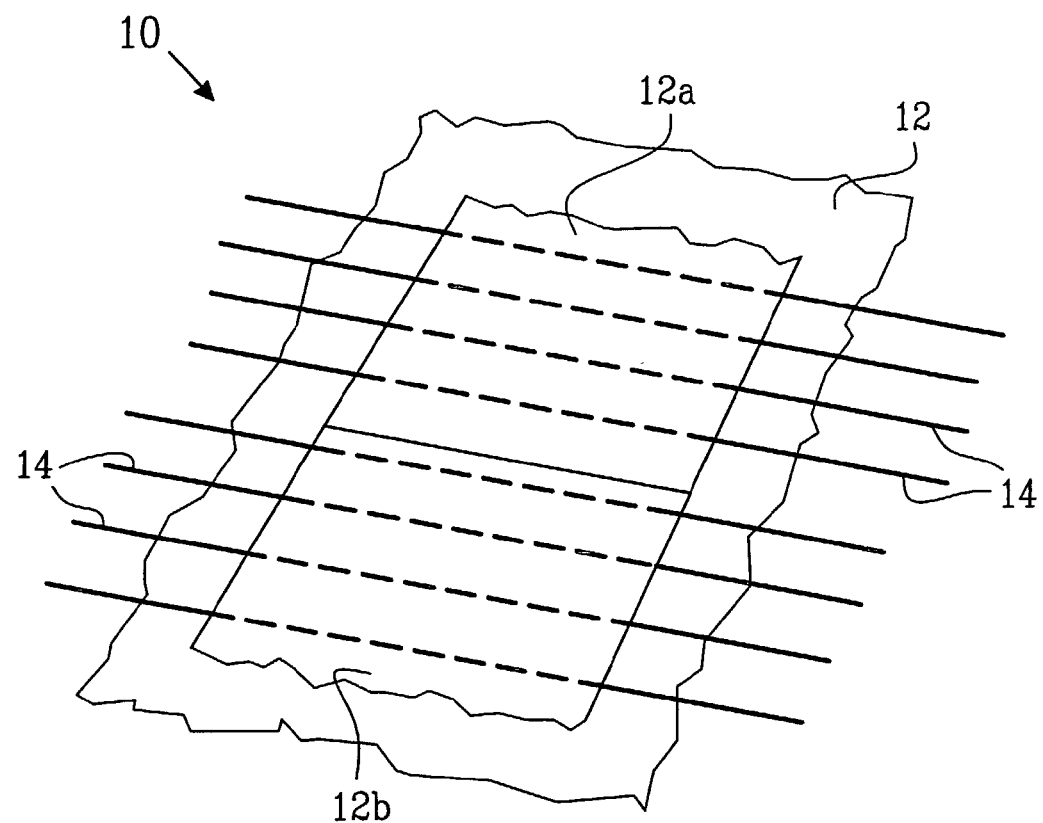
FIG. 5 is a schematic perspective view of a portion of an elasticized web according to a further embodiment of the present invention.

In embodiments having more than two gatherable substrates, the elasticized web may comprise a common first gatherable substrate 12 affixed to multi-strand elastic yarns 14 and two or more gatherable substrates overlying the first gatherable substrate and the elastic yarns. As is illustrated in FIG. 5, the two or more gatherable substrates 12a, 12b may be arranged adjacent each other in the plane of the substrates. Thus, if different materials are selected for the two or more gatherable substrates, an elasticized web is attainable having different surface characteristics across the web. It is therefore conceivable that one substrate 12a be a high friction material while the adjacent substrate 12b be an ordinary nonwoven material. Another possibility is that one substrate 12a be a liquid and/or vapor permeable nonwoven material while the adjacent substrate 12b be a liquid and/or vapor impermeable nonwoven. A further conceivable embodiment is the above-described FIG. 3 embodiment in which a second gatherable substrate of one of the above-mentioned materials is arranged adjacent and in the same plane as the folded over region 22. Yet another possible embodiment is one in which one or more of the gatherable substrates be constituted by an elastic laminate, for example an elastic nonwoven laminate as disclosed in, e.g., EP-B-0 713 546. Alternatively, or in combination with the above-described embodiments, a multi-substrate web of the present invention may include any number of gatherable substrates overlying each other.

Irrespective of the number of gatherable substrates included in the elasticized web of the present invention, the web must comprise an adequate number of first fixation locations 16. The distribution density of the fixation locations will be dependent on the constituent materials of the elasticized web, as well as the intended application of the web. Nevertheless, advantageous embodiments have been attained in which the number of first fixation locations is greater than one, and wherein the first fixation locations are spaced along the multi-strand elastic yarn by from 0.2 to 25 mm, preferably 0.2 to 10 mm, more preferably 0.5 to 5 mm and most preferably 0.5 mm to 3 mm.

Figure 6:
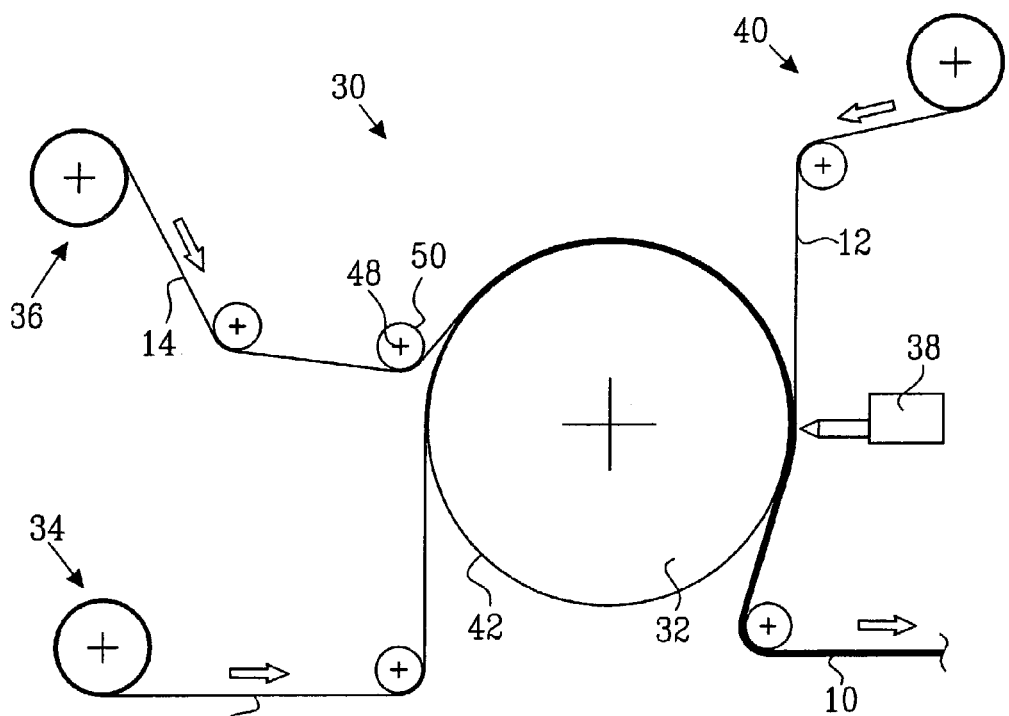
FIG. 6 is a schematic end view of apparatus according to the present invention.

Various methods for manufacturing the above-described elasticized webs and apparatus suitable therefor will be described in the following with particular reference to FIG. 6. In FIG. 6, reference numeral 30 generally denotes apparatus in accordance with the present invention. In its most general form, the apparatus 30 comprises a fixation station 32 which, in the preferred illustrated embodiment, is in the form of a rotatable drum having a peripheral surface. It will be apparent from the following description, however, that the fixation station may be stationary and may, for example, be in the form of a flat or curved plate.

The apparatus further comprises first feeding means, generally denoted by 34, for feeding a first gatherable substrate 12 to the fixation station. Normally, the first gatherable substrate is delivered on a roll and the first feeding means comprises means for drawing the substrate from the roll. In the case in which the fixation station is a rotatable drum, rotation of the drum may be used to draw the substrate from its roll. The apparatus also includes second feeding means, generally denoted by 36, for feeding one or more multi-strand elastic yarns 14 to the fixation station 32. Such means are well known in the art and can typically include Textrol Tension Control™ and BTSR™ equipment. As such, this equipment will not be described here in any greater detail. The multi-strand elastic yarns may either be fed to the fixation station 32 under tension, i.e. in an elongated condition, or tension may be imparted to the yarns upon arrival at the fixation station. So that the apparatus can achieve at least partial delamination of the elastic yarn, a source of energy 38 is associated with the fixation station. In this respect, the expression "associated with" means that the source of energy is located with respect to the fixation station such that the desired result, i.e. at least partial delamination, is attainable when the source of energy is energized. This at least partial delamination occurs at first fixation locations, i.e. those regions along the elastic yarn at which the gatherable substrate and the yarn are to be joined.

The apparatus further includes means, hereinafter termed displacement means, for causing a portion of the first gatherable substrate to pass between strands of the multi-strand elastic yarn at each first fixation location. In the illustrated embodiment, the source of energy 38 serves both to delaminate the elastic yarn and as displacement means. Thus, the source of energy preferably comprises pressurizing means, i.e. means for subjecting the elastic yarn 14 to pressure which, together with the tension in the elastic yarn, causes the multi-strand elastic yarn to at least partially delaminate. A particularly preferred source of energy is an ultrasonic device, for example VE20 CS equipment manufactured by Herrmann.

For producing elasticized webs having a plurality of gatherable substrates, feeding means for each substrate is required. Thus, in the embodiment illustrated in FIG. 6, third feeding means, generally denoted by 40, are provided for feeding a second gatherable substrate to the fixation station. Since the second gatherable substrate will overlie the first gatherable substrate with the elastic yarn between the two substrates, the third feeding means 40 supplies the second substrate to the fixation station downstream of the second feeding means 36.

Figure 7:
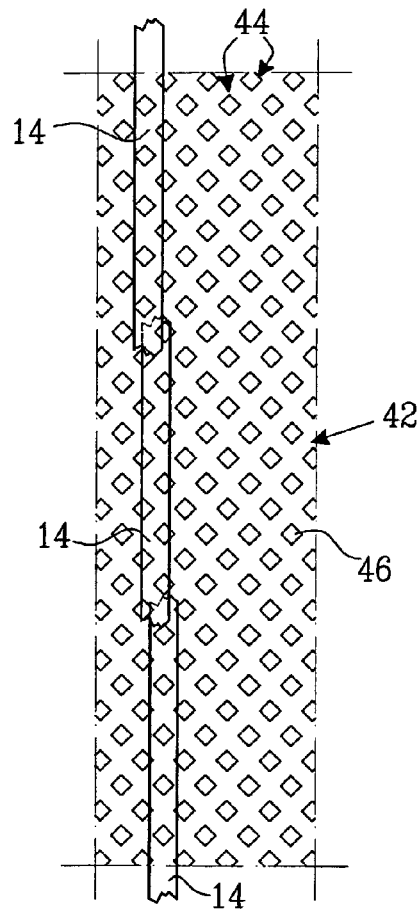
FIG. 7 is a schematic view on a magnified scale of a patterned surface for use in the apparatus of FIG. 6.

So as to define the actual locations or zones at which the first fixation locations 16 will be formed, the fixation station 32 preferably comprises a patterned surface 42. In the illustrated embodiment in which the fixation station is in the form of a rotatable drum, the patterned surface 42 is constituted by the peripheral surface of the drum. An example of a planar patterned surface is illustrated in FIG. 7. The patterned surface comprises raised heels 44, with each raised heel having a weld surface 46 against which the first gatherable substrate (not shown in FIG. 7) is made to lie. The actual surface area of the weld surfaces 46 and the spacing between the raised heels 44 is selected according to, amongst other things, the diameter of the elastic yarn 14 in its tensioned state. The shape of the weld surface 46 is not critical and is normally dictated by the manufacturing method for the patterned surface 42. Accordingly, the shape of the weld surface may be quadratic, rectangular, circular, oval, polygonal, or the like. As is schematically shown in FIG. 7, the distribution density of the raised heels 44 should be sufficient to ensure that, irrespective of the placement of the elastic yarn 14 with respect to the fixation station, an adequate number of first fixation locations 16 will be attained along the yarn. In FIG. 7, the elastic yarn is elongated 200%, i.e. to thrice its non-tensioned length. For an elasticized web which is to be used in a garment, it has been shown that the following weld surface area intervals are satisfactory, namely from 0.0025 $mm^2$ to 0.25 $mm^2$, preferably from 0.0064 $mm^2$ to 0.09 $mm^2$, more preferably from 0.0081 $mm^2$ to 0.04 $mm^2$, and most preferably from 0.0081 $mm^2$ to 0.0225 $mm^2$. In a corresponding manner, the raised heels 44 may be separated by a distance of from 0.1 mm to 1.0 mm, preferably from 0.1 mm to 0.5 mm, and most preferably from 0.15 mm to 0.25 mm. It has also been shown that the following heights of the heels 44 are satisfactory, namely from 0.05 mm to 2.0 mm, preferably from 01 mm to 1.0 mm, and most preferably from 0.1 mm to 0.5 mm. In practice, it has been generally found that, when affixing an elastic yarn 14 to a thicker substrate 12, it is necessary to use a correspondingly higher heel.

A considerable advantage offered by the apparatus of the present invention is that elasticized webs can be produced having elastic yarns which are very closely spaced. It will be apparent from FIG. 7 that the minimum spacing between adjacent elastic yarns will be dependent on the size and distribution density of the raised heels in relation to the diameter of the elastic yarn. In order to ensure accurate alignment of the elastic yarns, the second feeding means 36 of the apparatus according to the present invention may comprise a guide roller 48 having a peripheral surface 50, with the guide roller 48 being arranged substantially parallel to the rotatable drum 32. By providing the peripheral surface 50 of the guide roller 48 with a plurality of circumferentially extending grooves for the elastic yarns, accurate spacing between the elastic yarns is achieved. Such an arrangement provides for a rectilinear parallel arrangement of elastic yarns on the gatherable substrate(s).

The apparatus of the present invention is also eminently suitable for providing elasticized webs in which the elastic yarn is arranged in a curved manner. To achieve this, the second feeding means 36 comprises axial displacement means for displacing the elastic yarn axially with respect to the rotatable drum 32. Suitable such axial displacement means are disclosed in WO-A-89/09550, the contents of which are hereby incorporated by reference. In accordance with said document, grooves on a guide roller for elastic yarns wander along the roller during rotation of the roller to thereby lay the elastic yarns in a curved path over the substrate.

Since the apparatus of the present invention is to be capable of fixating two thermobondable gatherable substrates to a plurality of elastic yarns simultaneously, it will be apparent that the source of energy 38 must extend a distance in the cross direction which is considerably greater than the diameter of a tensioned elastic yarn 14. This implies that, for apparatus having a patterned surface for example as shown in FIG. 7, a plurality of thermobonded points of juncture will be created between the two gatherable substrates in regions bordering each multi-strand elastic yarn. The skilled person will appreciate that, by providing different patterned surfaces 42, elasticized webs can be produced having different bonding patterns.

Figure 8:
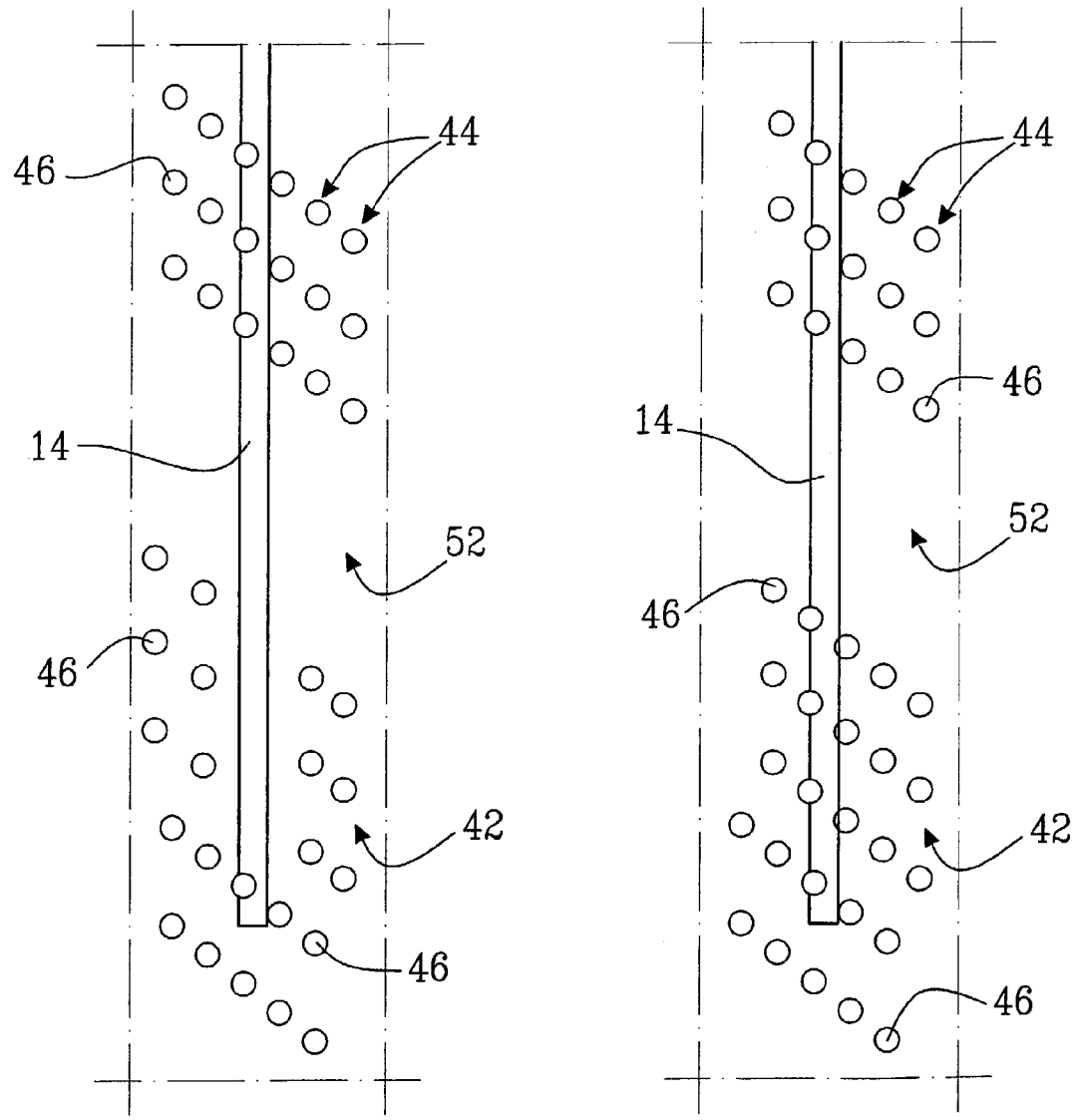
FIG. 8 is a schematic view similar to FIG. 7, though illustrating two further possible patterned surfaces for use in the apparatus of FIG. 6.

Thus, and with reference to FIG. 8, the present invention also contemplates the provision of a patterned surface 42 of the fixing station 32 in which the distribution density of the raised heels 44 varies over the surface area of the patterned surface. As will be apparent from the right-hand elastic yarn 14 illustrated in FIG. 8, the patterned surface 42 may comprise one or more regions 52 along the length of the yarn in which no raised heels are present. This implies that the elasticized web produced using this patterned surface will have regions along the length of the elastic yarn at which no bonds are present. Accordingly, the elastic yarn will be able to move independently of the substrate or substrates in such regions. A typical application for such a bonding pattern is in so-called standing gathers in absorbent articles such as diapers in which at least one elastic yarn is provided between a topsheet and a backsheet and is bonded at its end regions to either or both of the topsheet and backsheet. In the region along the elastic yarn in which no bonding is present, the elastic yarn tends to lift the topsheet from the backsheet to thereby form a raised barrier. The skilled person will also recognize that this aspect of the present invention may be useful in "snap-back" applications, i.e. where no attachment of an end region of a pre-stretched elastic yarn to a substrate is desired.

With reference to the left-hand elastic yarn 14 illustrated in FIG. 8, it will be apparent that the distribution density of the raised heels 44 may also be varied laterally of the elastic yarn. In other words, the patterned surface 42 may have selected regions, each having a different raised heel distribution density. The selected regions may be along the elastic yarn, lateral to the elastic yarn, or both. This implies that the elasticized web formed using such a patterned surface will have regions of differing properties. For example, where the distribution density is relatively low, the substrate will feel softer than in regions in which the distribution density is relatively high. The patterned surface between elastic yarns may be provided with a raised heel distribution which imparts a desired pattern on the elasticized web, irrespective of the raised heel distribution along the elastic yarns. The pattern between the elastic yarns may be purely decorative or it may depict an advertisement, or the like. It is also conceivable that the raised heels be provided with varying shapes of weld surfaces 46 in different regions of the patterned surface 42.

In a further embodiment of the apparatus according to the invention, the second feeding means 36 may be arranged such that various of the elastic yarns 14 are supplied to the fixation station 32 at differing tensions. This implies that the finished product, i.e. the elasticized web 10, will comprise elastic yarns having differing amounts of tension. In this manner, selected regions of the elasticized web can be provided with differing degrees of elasticity.

Due to the fact that the apparatus described above is capable of affixing an elastic yarn to a substrate substantially instantaneously, i.e. once the elastic yarn is affixed to the substrate at a certain fixation location, the region of the elastic yarn corresponding to that fixation location does not change its position relative to the substrate, elasticized webs can be produced in which the tension in each elastic yarn can be varied along its length. This has been very difficult to achieve when using adhesive to bond an elastic yarn to a substrate since the adhesive generally does not affix the elastic yarn sufficiently quickly to prevent the tension in the yarn tending to even out either side of the fixation location. The ability to provide regions of different elastic tension along the same yarn is highly useful when elastifying particular regions of a disposable absorbent article such as a diaper. With the present invention, it is possible to e.g. vary the tension around the waist region of the diaper such that, for example, greater tension is provided in the hip region than across the stomach region. Similarly, the tension in leg cuff elastic can be varied to ensure optimum fit and comfort.

In order to effect variation of the tension along an elastic yarn, the apparatus 30 of FIG. 6 may be provided with any suitable tension variation means. Since the tension in the elastic yarn 14 which is to be affixed to the substrates 12 will be governed by the surface velocity of the rotatable drum of the fixation station 32 with respect to the supply velocity of the elastic yarn, the tension in the elastic yarn can be increased by either briefly effectively braking the second feeding means 36 or briefly increasing the rotational speed of the drum of the fixation station. As mentioned previously, the second feeding means 36 may include Textrol Tension Control™ or BTSR™ equipment, and this equipment can be readily adapted to vary the tension in each elastic yarn between selected fixation locations.

The above-described apparatus may be used for carrying out the method of manufacturing an elasticized web 10, which web comprises a first gatherable substrate 12 and a multi-strand elastic yarn 14 affixed to the substrate 12 at a number of first fixation locations 16. The method comprises the steps of introducing the multi-strand elastic yarn 14 to the first gatherable substrate 12 such that the multi-strand elastic yarn becomes elongated under a tensioning force; subjecting the multi-strand elastic yarn 14 and the first gatherable substrate 12 at each first fixation location 16 to a source of energy sufficient to cause at least partial delamination of the multi-strand elastic yarn, and causing a portion of the first gatherable substrate to pass between strands 18 of the multi-strand elastic yarn at each first fixation location.

For an elasticized web comprising two gatherable substrates, the method according to the invention comprises the steps of introducing the multi-strand elastic yarn 14 to the first and second gatherable substrates 12 such that the multi-strand elastic yarn becomes elongated under a tensioning force and passes between the gatherable substrates; subjecting the multi-strand elastic yarn and the gatherable substrates at each first fixation location 16 to a source of energy sufficient to cause at least partial delamination of the multi-strand elastic yarn, and causing a portion of at least one of the first and second gatherable substrates to pass between strands of the multi-strand elastic yarn at each first fixation location.

Advantageously, the elastic yarn is elongated from 25% to 500%, preferably from 50% to 400%, more preferably from 75% to 350%, even more preferably from 100% to 300% and most preferably about 200%, of its non-tensioned length.

Although the elasticized web produced according to the above methods may be directly wound under tension onto a reel, it may be beneficial under certain circumstances to store the elasticized web in a relaxed condition. Accordingly, in an embodiment of the methods according to the present invention, after the step of causing a portion of at least one of the first and/or second gatherable substrates to pass between strands of the multi-strand elastic yarn at each first fixation location, the tensioning force in the multi-strand elastic yarn is released.

In another preferred embodiment of the methods of the present invention, the portion of the first and/or second gatherable substrate is caused to pass between strands of the multi-strand elastic yarn as a result of melting of a thermally bondable component of the respective gatherable substrate(s). This melting may be attained using an ultrasonic source of energy, e.g. the same source as used to at least partially delaminate the elastic yarn 14.

For those applications in which it is desired to vary the tension in the elastic yarn between selected fixation locations along the yarn, the method differs from those mentioned above in that the step of introducing the multi-strand elastic yarn 14 to either the first gatherable substrate 12 or the first and second gatherable substrates 12 includes introducing the multi-strand elastic yarn such that the yarn becomes elongated under a variable tensioning force, and the method further includes the step of varying the variable tensioning force between selected first fixation locations.

By carrying out the above methods using the preferred apparatus of the present invention in which a rotatable drum is employed as the fixation station, continuous production of an elasticized web can be easily attained. In test procedures conducted by the applicant using the equipment and materials listed below line speeds of greater than 200 m/min were achieved.

The prototype equipment comprised a 220 mm diameter rotatable drum having a surface pattern as shown in FIG. 7. The ultrasonic equipment was of the type VE 20 CS-KE-ST supplied by Herrmann and consisted of a KHS 20/4000 converter, a Ti/20 booster at 1:2, and an MS 161/45/16 CSI horn at 1:2.3. tests were performed on different nonwoven materials of 120 mm width. The nonwoven materials included Lutrasil 2017 (spunbond) 17 g/sqm, Holmestra N7W (carded) 20 g/sqm and Fibertex (SMMS) 12 g/sqm. LYCRA® XA® elastic yarn of 540 dtex and 800 dtex, type 151 C, 6M2xx, elongated 200%, was used. In each case, fixation of the elastic yarns to the gatherable substrates was achieved without the use of adhesives.

Elasticized webs of the present invention may be used in numerous applications. A particularly beneficial area of use is in garments such as disposable absorbent articles. Such articles may include diapers, incontinence protection garments, sanitary napkins, panty shields and the like. Other areas of use include curtains, drapes and bedding.

In the following, several disposable absorbent articles will be described to exemplify some, though not all, conceivable applications of the elasticized web of the present invention. Thus, and with reference to FIGS. 9 to 12, various disposable absorbent articles according to the present invention are generally denoted by reference numeral 54. Each article 54 comprises an absorbent structure 56 extending about a longitudinal axis L. The absorbent structure 56 has a transverse axis T dividing the absorbent structure into a front panel 58 terminating in a front end region 60 and a rear panel 62 terminating in a rear end region 64. When the absorbent article 54 is worn, the front panel 58 is intended to overlie the abdominal area of the wearer and the rear panel 62 is intended to overlie the buttocks area. The absorbent structure also has a crotch region 66 extending between the front end region 60 and the rear end region 64. The absorbent structure is delimited by opposed longitudinal edges 68 and opposed transverse edges 70. Typically, the absorbent structure further comprises an absorbent core 72 located primarily in the crotch region 66, with the absorbent core being sandwiched between a liquid pervious topsheet 74 and a generally liquid impervious backsheet 76.

The absorbent core 72 may comprise any conventional material suitable for absorbing discharged bodily wastes. Examples of such material include cellulosic fluff pulp, tissue layers, highly absorbent polymers (so-called superabsorbents), absorbent foam materials including hydrogel-foam material, absorbent nonwoven materials or the like. Typically, the absorbent core may comprise a cellulosic fluff pulp combined with one or more types of superabsorbent material in powder, granular, flake, fiber, foam or film form. If desired, the absorbent core may comprise a layered structure of different material with different properties with respect to liquid acquisition capacity, liquid distribution capacity and storage capacity. Since the person skilled in the art is familiar with such layered structures, they will not be described here in any greater detail.

The liquid permeable topsheet 74 can consist of a nonwoven material, e.g. spunbonded, meltblown, carded, hydroentangled, wetlaid, etc. Suitable nonwoven materials can be composed of natural fibers, such as woodpulp or cotton fibers, manmade fibers, such as polyester, polyethylene, polypropylene, viscose, etc. or from a mixture of natural and manmade fibers. The topsheet material may further be composed of tow fibers, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and be readily penetrated by body fluid, e g urine or menstrual fluid, and display low wetback, or rewetting, properties.

The liquid impermeable backsheet 76 may consist of a thin plastic film, e.g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapor to escape from the absorbent core, while still preventing liquids from passing through the backsheet material.

The topsheet 74 and the backsheet 76 have a somewhat greater extension in the plane than the absorbent core 72 and extend beyond the edges thereof. The layers 74 and 76 may be connected to each other within their overlapping portions, for example by gluing or welding by heat or ultrasonic. The topsheet and/or the backsheet may further be attached to the absorbent core by any method known in the art, such as adhesive, heat-bonding etc. The absorbent core may also be unattached to the topsheet and/or the backsheet.

Figure 9:
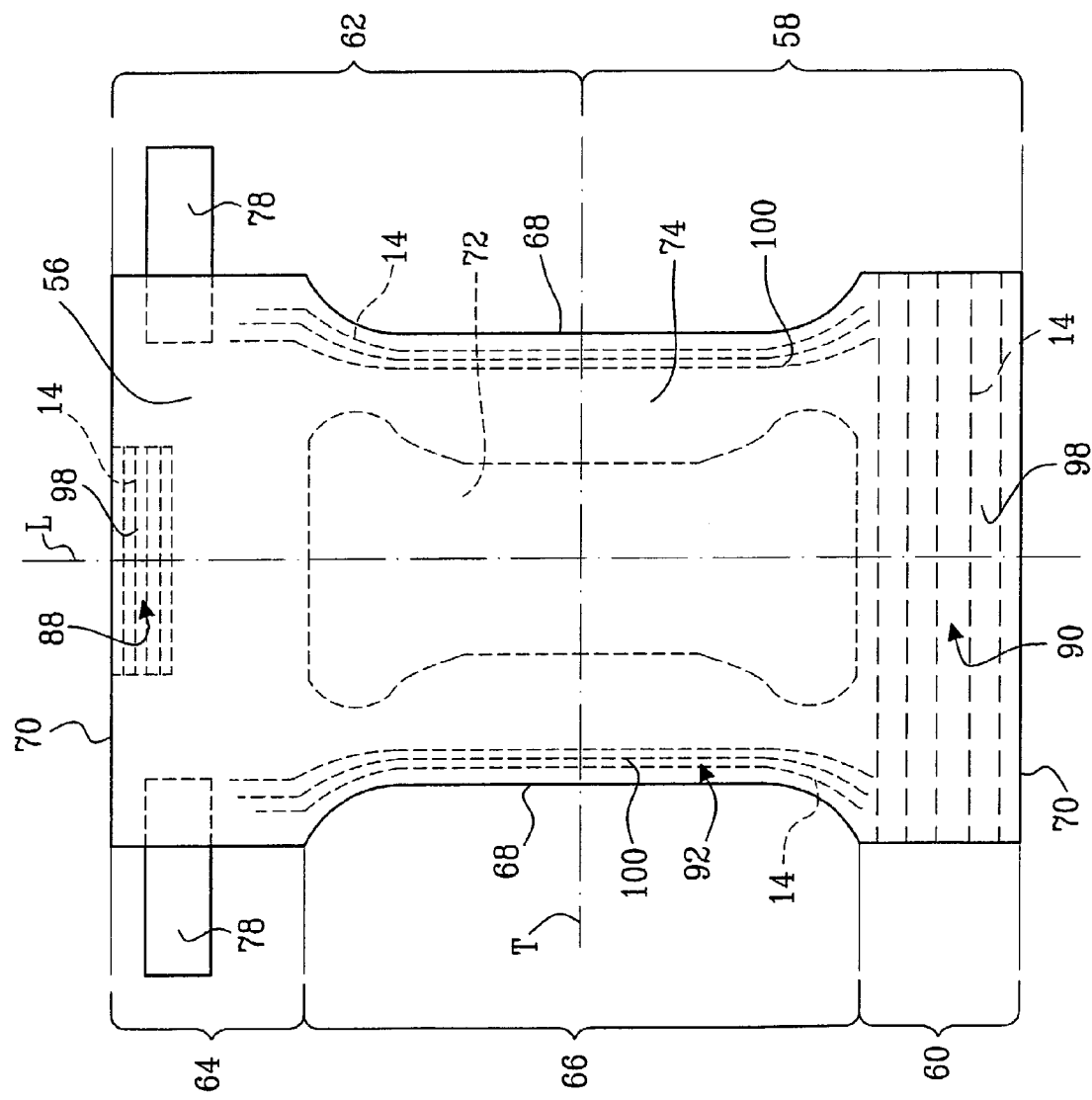
FIG. 9 is a schematic plan view of a first embodiment of a disposable absorbent article according to the present invention.
Figure 10:
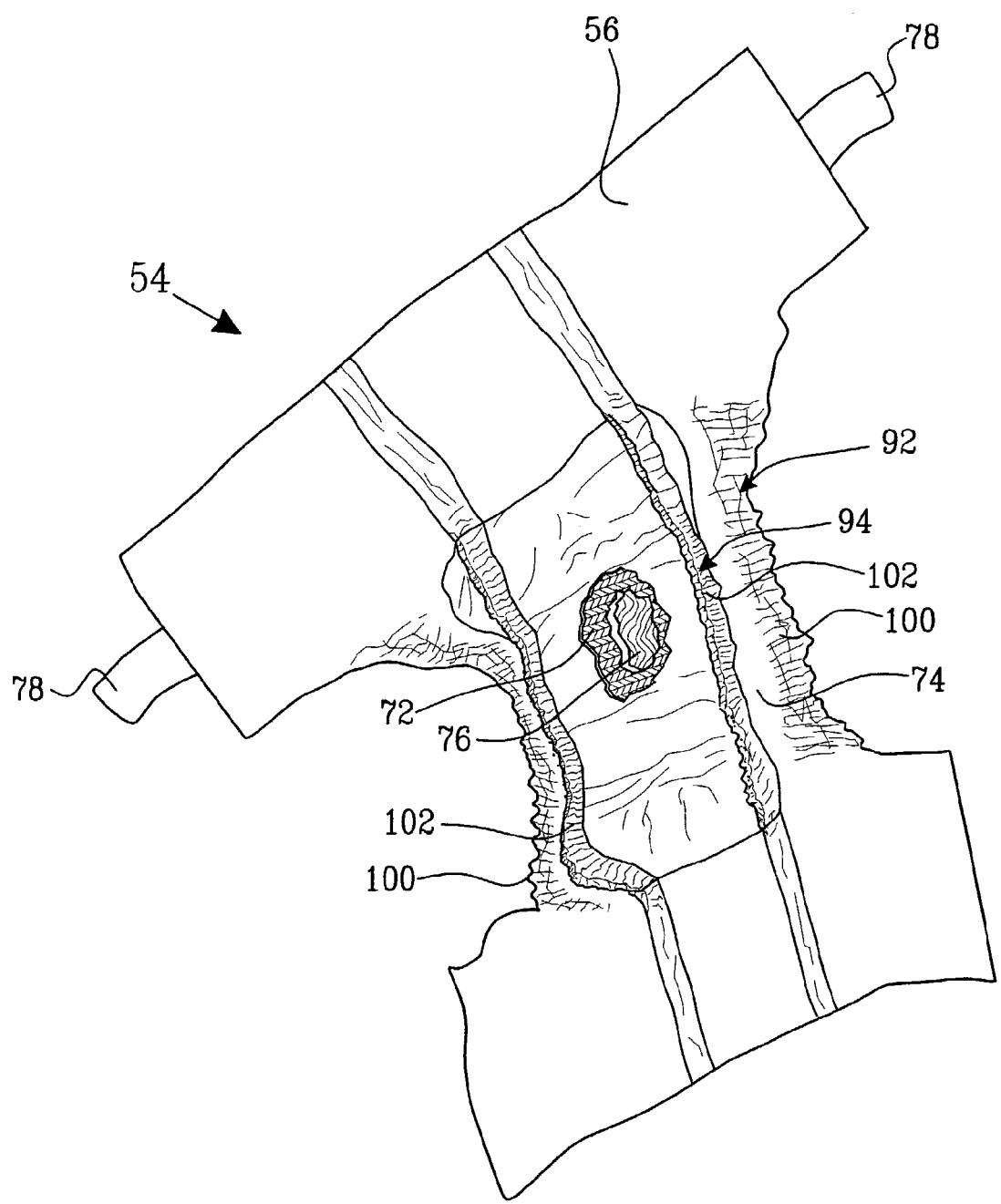
FIG. 10 is a schematic perspective view of the disposable absorbent article of FIG. 9 partially cut away.

The disposable absorbent article illustrated in FIGS. 9 and 10 is in the form of a diaper. As such, it comprises fastening means for securing the front and rear end regions to each other to thereby secure the diaper around the waist of a wearer. To this effect, the rear end region 64 is provided along its opposed longitudinal edges with a pair of tape fasteners 78. The tape fasteners are intended to co-operate with complementary receiving means located on the backsheet 76 in the front end region 60 of the absorbent structure 56. The fastening means may be constituted by any conventional fastening system, such as adhesive tapes, hook-and-loop systems, button and button-hole systems, press stud and popper arrangements, and the like.

Figure 11:
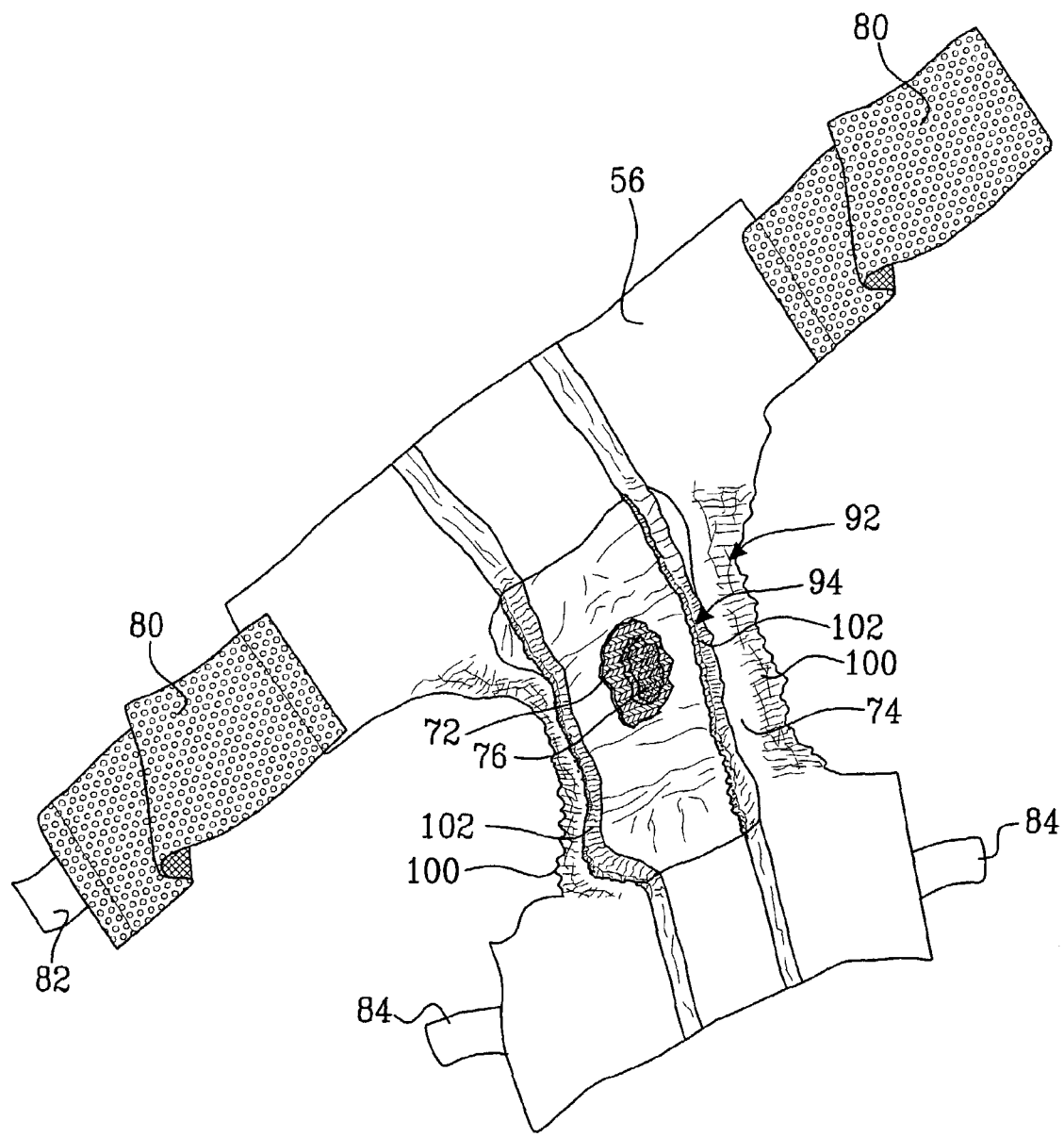
FIG. 11 is a schematic perspective view of a second embodiment of a disposable absorbent article according to the present invention.

The disposable absorbent article illustrated in FIG. 11 is in the form of a belted absorbent article. These articles are generally worn by adults and may be adapted for both incontinence and general use. In contrast to a conventional diaper, a belted absorbent article is provided with two belt halves 80 extending from the lateral sides of the rear end region 64 generally parallel to the transverse axis T of the absorbent structure 56. The belt halves 80 are intended to be placed around the waist of a wearer and fastened using any suitable fastener 82. The front end region 60 is provided with suitable fastening means 84, for example in the form of a pair of hook tabs or patches, to releasably secure the front panel 58 to the thus fastened belt halves, thereby retaining the belted absorbent article around the waist of a wearer. The belt halves themselves may be of any suitable construction and material and may comprise a laminate of a thin plastics film overlaid with a nonwoven material.

Figure 12:
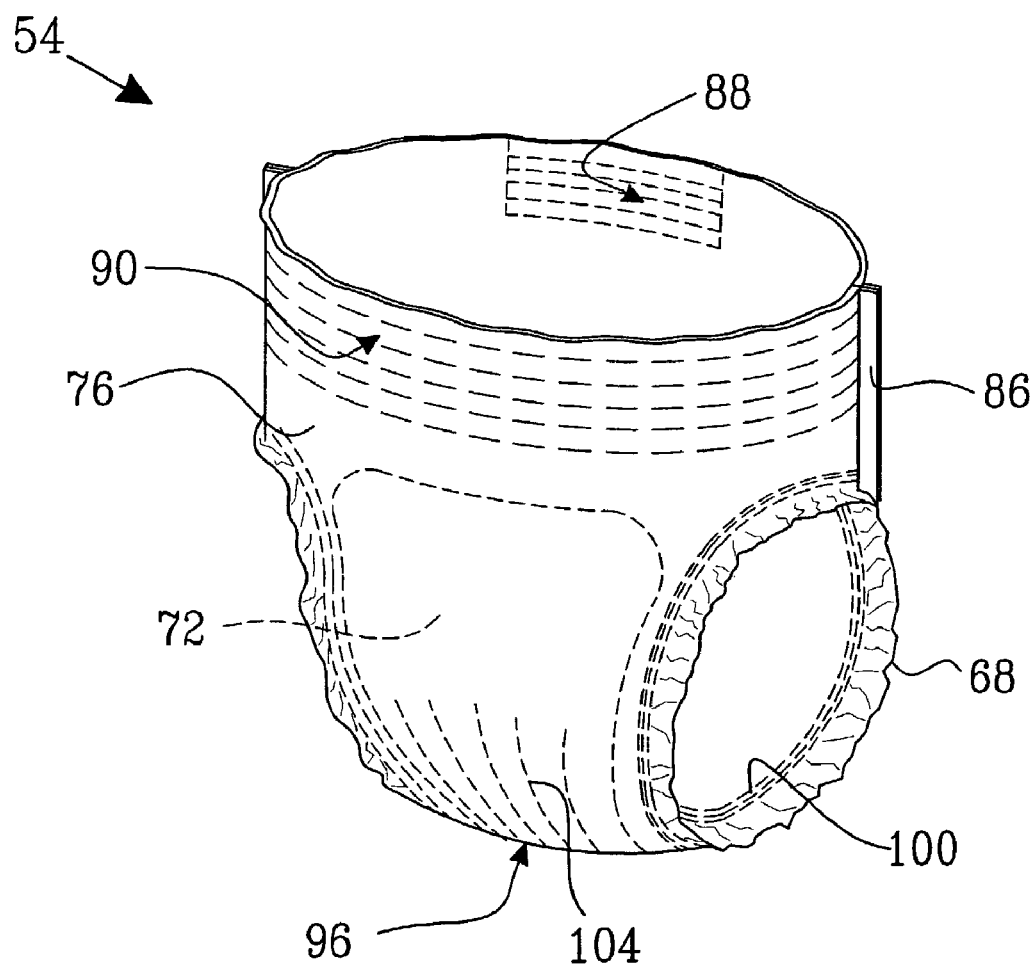
FIG. 12 is a schematic perspective view of a third embodiment of a disposable absorbent article according to the present invention.

The disposable absorbent article illustrated in FIG. 12 is in the form of a shorts-type diaper. In contrast to a conventional diaper, the front and rear end regions 58, 60 of a shorts-type diaper are initially secured to each other by means of rupturable side seams 86 to thereby provide a garment which can be drawn up on a wearer in the same manner as a normal undergarment.

In accordance with the present invention, and as will be described in greater detail in the following, the absorbent structure 56 of the disposable absorbent article (be it a conventional diaper, belted absorbent article, shorts-type diaper or any other absorbent article falling within the scope of the appended claims) includes at least one region 88, 90, 92, 94, 96 comprising the elasticized web as described earlier. As can be gleaned from the present description, such an elasticized web comprises at least one gatherable substrate and at least one multi-strand elastic yarn 14.

Thus, and with particular reference to FIG. 9, reference numerals 88 and 90 generally denote a first and a second region comprising the elasticized web of the present invention in which the at least one multi-strand elastic yarn 14 extends in a direction having a component parallel to the transverse axis T. By the expression "having a component parallel to the transverse axis", it is meant that the multi-strand elastic yarn 14 in the region in question has a length which extends non-perpendicularly to the transverse axis T. Thus, although the elastic yarns 14 illustrated in the first and second regions 88, 90 are shown as extending substantially parallel to the transverse axis T, it is to be understood that these yarns, or selected lengths thereof, may be oriented in any direction which is non-perpendicular to the transverse axis. The first and second regions 88, 90 constitute at least a part, though conceivably all, of a waist elastic structure 98 of the absorbent article. In the illustrated embodiment, the first region 88 constitutes a local elastification of the rear end region 64 and may comprise a plurality of closely spaced elastic yarns 14. The second region 90 constitutes an elastification of substantially the entire front end region 60. This is achieved by providing a plurality of relatively widely spaced elastic yarns 14 extending substantially the entire distance between the longitudinal edges 68. The gatherable substrate of the elasticized web in the first and second regions is advantageously the backsheet 76 of the absorbent structure 56, though it is also conceivable that the gatherable substrate be two in number and is constituted by the backsheet 76 and the topsheet 74. Particularly as regards the second region 90, the elastic yarns 14 may extend in a wave-shaped manner across the front end region 60. Furthermore, the tension in each elastic yarn may vary at different points across the front-end region. In addition, or separately to the above-mentioned two possibilities, the elastic yarns may have differing tensions with respect to each other.

As generally denoted by reference numerals 92, 94 and 96, the absorbent structure 56 of the disposable absorbent article 54 may include a third and/or a fourth and/or a fifth region comprising the elasticized web of the present invention in which the at least one multi-strand elastic yarn 14 extends in a direction having a component parallel to the longitudinal axis L. By the expression "having a component parallel to the longitudinal axis", it is meant that the multi-strand elastic yarn 14 in the region in question has a length which extends non-perpendicularly to the longitudinal axis L. Thus, although the elastic yarns 14 illustrated in the third, fourth and fifth regions 92, 94, 96 are shown as extending substantially parallel to the longitudinal axis L, it is to be understood that these yarns, or selected lengths thereof, may be oriented in any direction which is non-perpendicular to the longitudinal axis.

The third region 92 constitutes at least a part, though conceivably all, of a leg elastic structure 100 in the crotch region 66 of the absorbent structure. Thus, the absorbent article displays two leg elastic structures 100, i.e. one adjacent each longitudinal edge 68 of the absorbent structure 56. The leg elastic structures 100 are intended to provide a sealing effect around the upper leg region of a wearer of the absorbent article to thereby reduce the risk of leakage of bodily discharges from the absorbent article. Advantageously, the gatherable substrate of the elasticized web in the third region 92 is constituted by the topsheet 74 of the absorbent structure 56, though it is also conceivable that the gatherable substrate be two in number and be constituted by both the topsheet 74 and the backsheet 76. The number of elastic yarns in each leg elastic structure 100 is selected depending on the width of elasticized margin it is desired to provide. Purely by way of example, the number of yarns may typically be between two and five.

The fourth region 94 comprising the elasticized web of the present invention is most clearly illustrated in FIGS. 10 and 11. In this region, the at least one multi-strand elastic yarn 14 constitutes at least a part, though conceivably all, of a standing gather structure 102 in the crotch region 66 of the absorbent structure 56. Typically, a disposable absorbent article will have two standing gather structures, one either side of the longitudinal axis L and located between the leg elastic structures 100. The gatherable substrate of the elasticized web in the fourth region 94 may be constituted by the topsheet 74 of the absorbent structure 56. By affixing remote ends of the elastic yarn or yarns of each standing gather structure 102 to the absorbent structure in the front end region 60 and rear end region 64 while the yarn or yarns are under a tensioning force, the elastic yarn or yarns will tend to contract once the tensioning force is removed, to thereby lift the topsheet to create a standing gather. Alternatively, a standing gather may be created by utilizing one or more separate elasticized webs attached to the topsheet 74 of the absorbent structure.

The fifth region 96 comprising the elasticized web of the present invention is illustrated by way of example in FIG. 12. In this region, the at least one multi-strand elastic yarn 14 constitutes at least a part of a crotch elastic structure 104 in the crotch region 66 of the absorbent structure 56. The crotch elastic structure serves to, amongst other things, encourage the absorbent article to adopt a bowl shape in the crotch region when the article is worn to thereby assist in retaining discharged bodily wastes. The crotch elastic structure 104 may be symmetrically placed with respect to the transverse axis T and the longitudinal axis L, though it is conceivable that the region be positioned to occupy a greater extent of the front panel 58 than the rear panel 62 or vice versa. The gatherable substrate of the elasticized web in the fifth region 96 is constituted by the backsheet 76 of the absorbent structure 56.

The invention has been described above by way of example only and it is to be understood that the invention may be varied in many ways within the scope of the appended claims. For example, a disposable absorbent article according to the present invention may comprise any number of the above-described first, second, third, fourth and fifth regions and any combination of such regions is contemplated. Furthermore, the skilled person will recognize that the present invention may be practiced on sanitary napkins and panty liners having a longitudinal axis and a transverse axis and in which the multi-strand elastic yarn may be arranged so as to extend in a direction having a component parallel to the longitudinal axis and/or the transverse axis.

What is claimed is:

1. An elasticized web, comprising:
   a first gatherable substrate; and
   a multi-strand elastic yarn affixed to said first gatherable substrate at a plurality of fixation locations when the elastic yarn is elongated under tension so that the first gatherable substrate is gathered when the tension on the elastic yarn is relaxed,
   wherein at each fixation location a portion of said first gatherable substrate passes between strands of said multi-strand elastic yarn.

2. The elasticized web as claimed in claim 1, wherein said first gatherable substrate includes a thermally bondable material and said portion of said first gatherable substrate includes a melted component of said first gatherable substrate.

3. The elasticized web as claimed in claim 1, wherein a region of said first gatherable substrate is folded over said multi-strand elastic yarn to form a pocket within which said multi-strand elastic yarn runs.

4. The elasticized web as claimed in claim 2, wherein said thermally bondable material is selected from the group consisting of a spunbond, air laid, wet laid, hydroentangled, needled, carded or meltblown nonwoven of polyester, polypropylene, and polyethylene.

5. The elasticized web as claimed in claim 2, wherein said thermally bondable material is a combination of polymers, the combination of polymers being mixed, in layers, or in a bi-component fiber.

6. The elasticized web as claimed in claim 5, wherein the combination of polymers includes polyethylene and polypropylene.

7. The elasticized web as claimed in claim 2, wherein said thermally bondable material is a thermoplastic elastomer of polyurethane in sheet or film form.

8. The elasticized web as claimed in claim 1, wherein said plurality of fixation locations is greater than one, and wherein said fixation locations are spaced along said multi-strand elastic yarn by from 0.2 to 25 mm.

9. The elasticized web as claimed in claim 1, wherein one or more of any of said substrates has a basis weight of from 5 to 80 g/m$^2$.

10. The elasticized web as claimed in claim 1, comprising a plurality of multi-strand elastic yarns.

11. An elasticized web, comprising:
    a first gatherable substrate;
    a multi-strand elastic yarn affixed to said first gatherable substrate at a plurality of fixation locations; and
    a plurality of multi-strand elastic yarns,
    wherein at each fixation location a portion of said first gatherable substrate passes between strands of said multi-strand elastic yarn, and
    wherein said plurality of multi-strand elastic yarns includes elastic yarns having differing amounts of tension.

12. The elasticized web as claimed in claim 10, wherein said plurality of multi-strand elastic yarns are substantially rectilinear and generally parallel to each other.

13. The elasticized web as claimed in claim 10, wherein said plurality of multi-strand elastic yarns follow a curved path.

14. The elasticized web as claimed in claim 1, wherein said first gatherable substrate is an elastic laminate.

15. A disposable absorbent article comprising an elasticized web as claimed in claim 1.

16. The article of claim 15, wherein said article is a sanitary napkin or a panty shield.

17. A disposable absorbent article for attachment around a waist of a wearer, said article comprising:
    an absorbent structure extending about a longitudinal axis and having a transverse axis dividing the absorbent structure into a front panel terminating in a front end region and a rear panel terminating in a rear end region, said absorbent structure having a crotch region extending between said front end region and said rear end region, the absorbent structure being delimited by opposed longitudinal edges and opposed transverse edges, wherein said absorbent structure includes at least one region comprising an elasticized web as claimed in claim 1.

18. The article as claimed in claim 17, wherein said multi-strand elastic yarn extends in a direction having a component parallel to said transverse axis.

19. A disposable absorbent article for attachment around a waist of a wearer, said article comprising:
    an absorbent structure extending about a longitudinal axis and having a transverse axis dividing the absorbent structure into a front panel terminating in a front end region and a rear panel terminating in a rear end region, said absorbent structure having a crotch region extending between said front end region and said rear end region, the absorbent structure being delimited by opposed longitudinal edges and opposed transverse edges, wherein said absorbent structure includes at least one region comprising an elasticized web, the elasticized web comprising a first gatherable substrate, and a multi-strand elastic yarn affixed to said first gatherable substrate at a plurality of fixation locations, wherein at each fixation location a portion of said first gatherable substrate passes between strands of said multi-strand elastic yarn,
    wherein said multi-strand elastic yarn extends in a direction having a component parallel to said transverse axis, and
    wherein said multi-strand elastic yarn constitutes at least a part of a waist elastic structure in said front end region or said rear end region of said absorbent structure.

20. The article as claimed in claim 19, wherein said waist elastic structure comprises said elasticized web, said first gatherable substrate of said elasticized web being a backsheet of said absorbent structure.

21. The article as claimed in claim 19, further comprising a topsheet and a backsheet, wherein said first gatherable substrate is said backsheet or said topsheet of said absorbent structure.

22. The article as claimed in any one of claim 17, wherein said multi-strand elastic yarn extends in a direction having a component parallel to said longitudinal axis.

23. A disposable absorbent article for attachment around a waist of a wearer, said article comprising:
    an absorbent structure extending about a longitudinal axis and having a transverse axis dividing the absorbent structure into a front panel terminating in a front end region and a rear panel terminating in a rear end region, said absorbent structure having a crotch region extending between said front end region and said rear end region, the absorbent structure being delimited by opposed longitudinal edges and opposed transverse edges, wherein said absorbent structure includes at least one region comprising an elasticized web, the elasticized web comprising a first gatherable substrate, and a multi-strand elastic yarn affixed to said first gatherable substrate at a plurality of fixation locations, wherein at each fixation location a portion of said first gatherable substrate passes between strands of said multi-strand elastic yarn, wherein said multi-strand elastic yarn extends in a direction having a component parallel to said longitudinal axis, and further comprising a leg elastic structure in said crotch region, wherein said multi-strand elastic yarn is at least a part of said leg elastic structure.

24. The article as claimed in claim 23, wherein said leg elastic structure comprises said elasticized web, said first gatherable substrate of said elasticized web being a topsheet of said absorbent structure.

25. The article as claimed in claim 24, further comprising a backsheet, a topsheet, and a second gatherable substrate, wherein said first gatherable substrate and said second gatherable substrate are each one of said backsheet and said topsheet.

26. The article as claimed in claim 22, further comprising a standing gather structure in said crotch region, wherein said multi-strand elastic yarn is at least a part of said standing gather structure.

27. The article as claimed in claim 26, wherein said standing gather structure comprises said elasticized web, and said first gatherable substrate of said elasticized web is a topsheet of said absorbent structure.

28. The article as claimed in claim 18, further comprising a crotch elastic structure in said crotch region, wherein said multi-strand elastic yarn is at least a part of said crotch elastic structure.

29. The article as claimed in claim 28, wherein said crotch elastic structure comprises said elasticized web, and said first gatherable substrate of said elasticized web is a backsheet of said absorbent structure.

30. The article as claimed in claim 17, wherein said article is selected from the group consisting of a child diaper, an adult diaper, a shorts-type diaper, a belted absorbent article and an incontinence garment.

31. The elasticized web as claimed in claim 1, comprising a plurality of multi-strand elastic yarns,
wherein said plurality of multi-strand elastic yarns includes elastic yarns having differing amounts of tension.

32. The elasticized web as claimed in claim 31, wherein said first gatherable substrate includes a thermally bondable material and said portion of said first gatherable substrate includes a melted component of said first gatherable substrate.

33. The elasticized web as claimed in claim 32, wherein said thermally bondable material is selected from the group consisting of a spunbond, air laid, wet laid, hydroentangled, needled, carded or meltblown nonwoven of polyester, polypropylene, and polyethylene.

34. The elasticized web as claimed in claim 32, wherein said thermally bondable material is a combination of polymers, the combination of polymers being mixed, in layers, or in a bi-component fiber.

35. The elasticized web as claimed in claim 34, wherein the combination of polymers includes polyethylene and polypropylene.

36. The elasticized web as claimed in claim 32, wherein said thermally bondable material is a thermoplastic elastomer of polyurethane in sheet or film form.

37. The elasticized web as claimed in claim 31, wherein said plurality of fixation locations is greater than one, and wherein said fixation locations are spaced along said multi-strand elastic yarn by from 0.2 to 25 mm.

38. The elasticized web as claimed in claim 31, wherein one or more of any of said substrates has a basis weight of from 5 to 80 g/m$^2$.

39. The elasticized web as claimed in claim 31, wherein said plurality of multi-strand elastic yarns follow a curved path.

40. The elasticized web as claimed in claim 31, wherein said first gatherable substrate is an elastic laminate.

41. A disposable absorbent article comprising an elasticized web as claimed in claim 31.

42. The elasticized web as claimed in claim 11, wherein said first gatherable substrate includes a thermally bondable material and said portion of said first gatherable substrate includes a melted component of said first gatherable substrate.

43. The elasticized web as claimed in claim 42, wherein said thermally bondable material is selected from the group consisting of a spunbond, air laid, wet laid, hydroentangled, needled, carded or meltblown nonwoven of polyester, polypropylene, and polyethylene.

44. The elasticized web as claimed in claim 42, wherein said thermally bondable material is a combination of polymers, the combination of polymers being mixed, in layers, or in a bi-component fiber.

45. The elasticized web as claimed in claim 44, wherein the combination of polymers includes polyethylene and polypropylene.

46. The elasticized web as claimed in claim 42, wherein said thermally bondable material is a thermoplastic elastomer of polyurethane in sheet or film form.

47. The elasticized web as claimed in claim 11, wherein said plurality of fixation locations is greater than one, and wherein said fixation locations are spaced along said multi-strand elastic yarn by from 0.2 to 25 mm.

48. The elasticized web as claimed in claim 11, wherein one or more of any of said substrates has a basis weight of from 5 to 80 g/m$^2$.

49. The elasticized web as claimed in claim 11, wherein said plurality of multi-strand elastic yarns follow a curved path.

50. The elasticized web as claimed in claim 11, wherein said first gatherable substrate is an elastic laminate.

51. A disposable absorbent article comprising an elasticized web as claimed in claim 11.

* * * * *